United States Patent [19]

Horrobin et al.

[11] Patent Number: 5,516,801

[45] Date of Patent: May 14, 1996

[54] FATTY ACID TREATMENT FOR ECTOPIC CALCIUM DEPOSITION

[75] Inventors: David F. Horrobin; Brenda E. Reynolds, both of Guildford, England

[73] Assignee: Scotia Holdings plc, Surrey, England

[21] Appl. No.: 365,171

[22] Filed: Dec. 28, 1994

Related U.S. Application Data

[63] Continuation of Ser. No. 109,482, Aug. 20, 1993, abandoned.

[30] Foreign Application Priority Data

Aug. 21, 1992 [GB] United Kingdom ............... 9217780
Aug. 21, 1992 [GB] United Kingdom ............... 9217781

[51] Int. Cl.$^6$ ................................................ A61K 31/20
[52] U.S. Cl. .................................................. 514/560
[58] Field of Search ............................ 514/558, 549, 514/560

[56] References Cited

U.S. PATENT DOCUMENTS

| | | |
|---|---|---|
| 4,816,483 | 3/1989 | Georgieva et al. |
| 4,855,136 | 8/1989 | Horrobin et al. ............... 424/602 |
| 5,318,991 | 6/1994 | Horrobin et al. ............... 514/560 |

FOREIGN PATENT DOCUMENTS

| | | |
|---|---|---|
| 0517425A1 | 12/1992 | European Pat. Off. . |
| WO87/06463 | 11/1987 | WIPO . |

OTHER PUBLICATIONS

Current Opinion in Gastroenterology vol. 8, No. 2, Apr. 1992.
J. Urology vol. 146, No. 1, Jul. 1991 Buck et al "The Protective Role of Eicosapentaenoic Acid . . . ".
J. Urology, vol. 149, No. 4, Apr. 1993 Burgess p. 441A.
J. Urology, vol. 149, No. 4, Apr. 1993 p. 499A Buck.

*Primary Examiner*—Raymond Henley, III
*Attorney, Agent, or Firm*—Nixon & Vanderhye

[57] ABSTRACT

Prevention and/or treatment of abnormal calcification in any tissue by the administration of (i) GLA and/or its EFA metabolites, and in particular the rapidly produced DGLA and/or (ii) EPA and/or its precursors, stearidonic acid and 20:4 n-3, and metabolites, docosahexaenoic acid (DHA) or docosapenmenoic acid (22:5 n-3), as such or in salt or other pharmacologically acceptable form. This is especially suitable for prevention or treatment of nephrocalcinosis and/or renal stones.

5 Claims, No Drawings

FATTY ACID TREATMENT FOR ECTOPIC CALCIUM DEPOSITION

This is a continuation of application Ser. No. 08/109,482, filed Aug. 20, 1993, now abandoned.

FIELD OF INVENTION

This invention relates to fatty acid treatments, and in particular to prevention and/or treatment of abnormal tissue calcification, and more particularly to treatment or prevention of nephrocalcinosis of the kidneys.

FATTY ACIDS

The pathways of conversion of the main series of polyunsaturated fatty acids in the body are as in Table 1 below:

TABLE 1

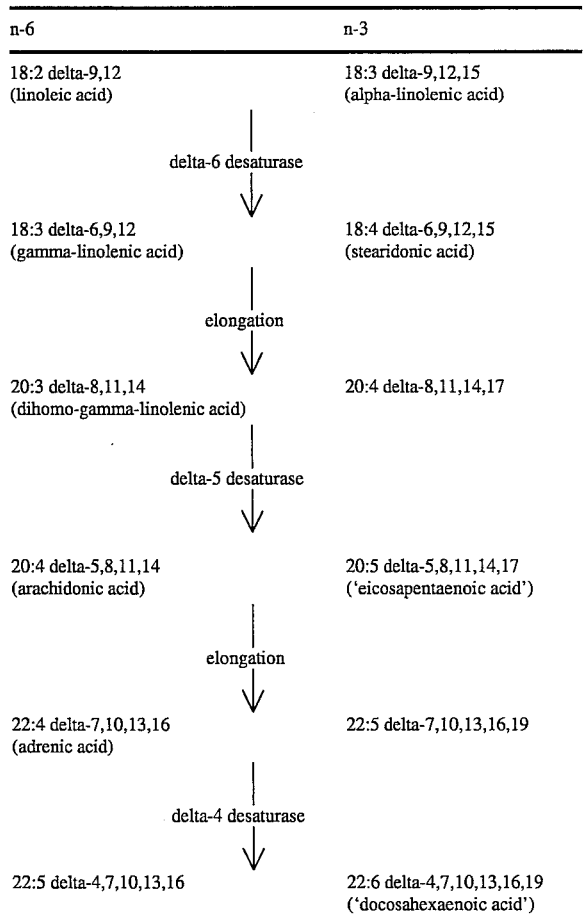

| n-6 | n-3 |
|---|---|
| 18:2 delta-9,12 (linoleic acid) | 18:3 delta-9,12,15 (alpha-linolenic acid) |
| 18:3 delta-6,9,12 (gamma-linolenic acid) | 18:4 delta-6,9,12,15 (stearidonic acid) |
| 20:3 delta-8,11,14 (dihomo-gamma-linolenic acid) | 20:4 delta-8,11,14,17 |
| 20:4 delta-5,8,11,14 (arachidonic acid) | 20:5 delta-5,8,11,14,17 ('eicosapentaenoic acid') |
| 22:4 delta-7,10,13,16 (adrenic acid) | 22:5 delta-7,10,13,16,19 |
| 22:5 delta-4,7,10,13,16 | 22:6 delta-4,7,10,13,16,19 ('docosahexaenoic acid') |

The above pathways are not normally reversible nor, in man, are n-3 and n-6 series acids interconvertible.

The acids, which in nature are of the all-cis configuration, are systematically named as derivatives of the corresponding octadecanoic, eicosanoic or docosanoic acids. e.g. delta-9,12-octadecadienoic acid or delta- 4,7,10,13,16,19 docosahexaenoic acid. but numerical designations such as, correspondingly, 18:2 n-6 or 22:6 n-3 are convenient. Initials, for example, EPA for the 20:5 n-3 acid (eicosapentaenoic acid) or DHA for the 22:6 n-3 acid (docosahexaenoic acid), are also used but do not serve when n-3 and n-6 acids of the same chain length and degree of unsaturation exist as for example with the 22:5 acids. Trivial names in more or less common use in the n-6 series are as shown. Of the n-3 series only 18:3 n-3 has a commonly used trivial name, alpha-linolenic acid, though the name stearidonic acid is coming into use for the 18:4 n-3 acid and the names eicosapentaenoic acid and docosahexanenoic acid as such are also used. The alpha isomer of linolenic acid was characterized earlier than gamma-linolenic acid and reference in the literature simply to linolenic acid, especially in the earlier literature, is to the alpha-acid.

ABNORMAL CALCIFICATION, DISCUSSION AND EXPERIMENTAL

Abnormal calcification may occur for a number of reasons, and may be primary causes of or secondary results of specific disease conditions. The deposition of calcium in the soft tissue (ectopic mineralization) is nearly always pathological and often its cause is unknown.

Where the circulating level of calcium is consistently high, mineralization of many soft tissues can occur. The tissues affected include blood vessels, cornea, conjunctivae, skin, brain and kidneys. In parathyroid insufficiency for example, calcification occurs in the basal ganglia and in the skin, whereas in primary or secondary hyperparathyroidism, calcification occurs in the blood vessels and periarticular tissues. Tumoral calcinosis is a condition in which ectopic mineralisation is characterised by the presence of large masses of calcium around the large joints. Calcification can occur in tissues affected by aquired connective tissue disorders such as scleroderma anti dermatomyositis, the former occurring sometimes in association with Raynaud's phenomena and telangiectases (CRST syndrome).

Radiation damage to brain microvasculature resulting from radiotherapy may lead to necrosis and calcification of surrounding tissue and grey matter.

Chondrocalcinosis is the formation of mineral outside the skeleton, commonly in joints. A number of diseases are associated with such calcium deposition e.g. chronic pyrophosphate arthropathy, acute calcific periarthritis (acute synovitis) and osteoarthritis.

Nephrocalcinosis or calcification of the kidney is a very common form of ectopic calcification. The commonest causes are hyperparathyroidism, hypervitaminosis D and chronic interstitial nephritis. Other causes include osteoporosis, sarcoidosis, renal tubular acidosis, the de Toni-Fanconi syndrome and destruction of bone by metastatic carcinoma.

Because of the widespread occurrence of soft tissue calcification in disease conditions, the applicants designed an animal model of ectopic calcification in the kidney to investigate the effects of treatment with 6-desaturated essential fatty acids of both the n-6 and n-3 series. 74 female PVG rats were divided into 7 groups as described below:

| | |
|---|---|
| Group 1 | Controls treated with 1.5 ml of 10% calcium gluconate daily for 10 days to induce nephrocalcinosis (n = 10); |
| Group 2 | Given eicosapentaenoic acid (EPA) 38 mg by gavage daily 4 days prior to and during 10 days of calcium gluconate administration as in 1 above (n = 10); |
| Group 3 | Given gammalinolenic acid (GLA) 66 mg plus EPA 60 mg as in 2 above (n = 10); |
| Group 4 | Given gammalinolenic acid 83 mg per day as in 2 above (n = 10); |
| Group 5 | Given 1 ml sunflower oil per day as in 2 above (n = 10); |
| Group 6 | Given 1 ml olive oil per day as in 2 above (n = 10); |
| Group 7 | Given only an i.p. injection of saline for 10 days |

-continued (n = 14).

The presence of calcification at day 15 was assessed qualitatively by histology using von kossa and alizarin staining and quantitatively by wet chemical spectroscopic analysis. The results are summarised below:

| Group | Calcium in Kidney mg/g dry weight | Significance |
| --- | --- | --- |
| 1. Control (treated) | 0.83 ± 0.51 | |
| 2. EPA | 0.10 ± 0.13 | *** |
| 3. GLA plus EPA | 0.19 ± 0.19 | *** |
| 4. GLA | 0.21 ± 0.16 | *** |
| 5. Sunflower Oil | 1.30 ± 0.97 | |
| 6. Olive Oil | 1.12 ± 0.55 | |
| 7. Control (untreated) | 0.15 ± 0.04 | *** |

These results indicate that both GLA and EPA individually or in combination can significantly decrease calcification of the kidney in rats even when circulating calcium levels are extremely high.

THE INVENTION

Based on the above, the invention in one aspect lies in the use of (i) GLA and/or its EFA metabolites, and in particular the rapidly produced DGLA and/or (ii) EPA and/or its precursors, stearidonic acid and 20:4 n-3, and metabolites, docosahexaenoic acid (DHA) or docosapentaenoic acid (22:5 n-3) for prevention and/or treatment of abnormal calcification of any tissue in both animals and humans. The abnormal calcification may be the primary cause of one of the diseases previously reviewed, or may result from another disease.

Alternatively, the invention may be regarded as lying in a method of, or preparation of a medicament for, treating or preventing abnormal calcification of any tissue in humans or in animals by administering (i) GLA and/or its EFA metabolites, and in particular the rapidly produced DGLA and/or (ii) EPA and/or its precursors, stearidonic acid and 20:4 n-3, and metabolites, docosahexaenoic acid (DHA) or docosapentaenoic acid (22:5 n-3).

As noted, GLA in the body is very rapidly converted to dihomo-gammalinolenic acid (DGLA); DGLA therefore has a very similar effect to GLA.

As discussed further below the essential fatty acids may be used as such or in any appropriate form, including but not limited to triglyceride, diglycefide, monoglyceride, free fatty acid, any appropriate ester, any appropriate salt including the lithium, sodium, potassium, zinc, magnesium or other salt, phospholipid, amide or any other pharmacologically acceptable form.

The preferred dose range is from 0.01 to 1,000 mg/kg/day, more preferably from 0.5 to 100 mg/kg/day, very preferably from 2 to 30 mg/kg/day of GLA or DGLA, and medicaments are readily prepared in dosage unit form to administer such amounts (related to a 70 kg human adult).

ROUTES OF ADMINISTRATION

Oral, parenteral (sub-cutaneous, intramuscular, intravenous or by any other appropriate route), enteral, topical in the form of appropriate EFA-containing ointments, creams, lotions, patches, etc. vaginal or rectal are among suitable routes of administration.

DERIVATIVES OF EFAs

As indicated above, the acids may be used as such or as pharmaceutically acceptable and physiologically equivalent derivatives as, for example, detailed herein for GLA and DGLA, and reference to any of the acids is to be taken as including reference to the acids when in the form of such derivatives. Equivalence is demonstrated by entry into the pathway quoted herein, as evidenced by effects corresponding to those of the acids themselves or their natural glyceride esters. Thus, indirect identification of useful derivatives is by their having the valuable effect in the body of the acid itself, but conversion can be shown directly by gas chromatographic analysis of concentrations in blood, body fat, or other tissue by standard techniques, for example those of Pelick et al, page 23, "Analysis of Lipids and Lipoproteins" Ed Perkins, American Oil Chemists Society, Champaign, Ill., U.S.A.

In outline the method is suitably that plasma samples (1 ml) are extracted with chloroform:methanol (2:1). The extract is filtered through sodium sulphate, evaporated to dryness, and taken up in 0.5 ml chloroform:methanol. The lipid fractions are separated by thin layer chromatography or silica gel plates. The phospholipid fraction, taken to reflect essential fatty acid contents most sensitively, is methylated using boron trifiuoride-methanol. The resulting methyl esters of the fatty acids are separated and measured using a Hewlett-Packard 5880 gas chromatograph with a six foot column packed with 10% Silar on Chromosorb WAW 106/230. The carder gas is helium (30 ml/min). Oven temperature is programmed to rise from 164° C. to 190° C. at 2° C./min. Detector temperature is 220° C. and injector temperature 200° C. Retention times and peak areas are automatically computed by Hewlett-Packard Level 4 integrator. Peaks are identified by comparison with standard fatty acid methyl esters.

DIETARY COMPOSITIONS

The invention is chiefly described in terms of methods of treatment and in the use of GLA or its metabolites and/or EPA or its metabolites in the preparation of pharmaceutical compositions, but it will be understood that the gamma-linolenic and other EFAs, being in the nature of dietary supplements, can be incorporated in a dietary margarine or other foodstuff and such are to be understood as within the term pharmaceutical composition or medicament herein (including the claims) when for the purposes set out.

If desired, pharmaceutical compositions may be produced for use in the invention by associating the natural or synthetic acids, as such or as derivatives, with an acceptable pharmaceutical vehicle. It is, however, at present convenient to provide at least GLA in the/brm of an available oil having a high GLA content, hence reference to "oils" herein.

One source of oils currently available is the seed of evening primrose species such as *Oenothera biennis L.* and *Oenothera lamarckiana*, the oil extract therefrom containing about 8 % GLA and about 72 % linoleic acid in the form of their glycerides, together with other glycerides (percentages based on total fatty acids). Other sources of GLA are borage species such as *Borago officinalis* which provide a richer source than *Oenothera* oil. Oils from the seeds of members of the *Ribes* family are also often rich in GLA. Recent studies on fungi which can be cultivated by fermentation promise a fungal oil source. Some algae also produce GLA and may be harvested or cultured. Synthesis is also possible.

The oil is extracted from the seed by one of the conventional methods of extraction such as cold pressure, screw pressure alter partially cooking the seed, or solvent extraction.

Fractionation of a typical sample of evening primrose oil as used in the work reported herein in the form of methyl esters shows the relative proportions:

| | |
|---|---|
| Palmitate | 6.15 |
| Stearate | 1.6 |
| Oleate | 10.15 |
| Linoleate | 72.6 |
| Gamma-linolenate | 8.9 |

The seed oil extracts referred to above can be used as such or can, for example, if desired, be fractionated to yield an oily composition containing the triglycerides of gamma-linolenic and linoleic acids as the main fatty acid: components, the gamma-linolenic acid content being, if desired, a major proportion. Seed oil extracts appear to have a stabilising effect upon DGLA if present.

GLA, EPA and the other EFAs or their derivatives or metabolites may be produced by any suitable method including chemical synthesis, fermentation (microbial or algal), extraction from animal, botanical or other source, agronomy or other methods as appropriate.

PHARMACEUTICAL PRESENTATION

As mentioned briefly above, the compositions are conveniently in a form suitable for oral, topical, parenteral or other route of administration in a suitable pharmaceutical vehicle, well known generally for any particular kind of preparation. Thus, for example, tablets, capsules, ingestible liquid or powder preparations can be prepared as required, and topical preparations also when the gamma-linolenic acid or other acids are absorbed through the skin. Injectable solutions of hydrolysed Oenothera or other oil may be prepared using albumin to solubilise the free acid. Emulsions and salts can also be administered by infusion or injection.

Advantageously, a preservative is incorporated into the preparation. Alpha-tocopherol in a concentration of about 0.1% by weight has been found suitable for the purpose and is one of a number of possible stabilisers well known in the field and including also for example ascorbyl palmitate and stearate.

It will be understood that the absolute quantity of active materials present in any dosage unit should not exceed that appropriate to the rate and manner of administration to be employed but on the other hand should also desirably be adequate to allow the desired rate of administration to be achieved by a small number of doses. The rate of administration will moreover depend on the precise pharmacological action desired.

The composition may also be in the form of whips, emulsions, suspensions, pessaries, suppositories, transdermal devices or any other appropriate forms.

EXAMPLES

The following are examples of compositions and their administration for the purposes discussed herein.

1. Administration of 100 mg to 2,000 mg of GLA per day in the form of soft or hard gelatin capsules or tablets providing:

a. 40 to 80 mg per capsule of GLA in the form of evening primrose oil.

b. 50–150 mg per capsule of GLA in the form of borage, blackcurrant, fungal or other appropriate oil.

c. 100–150 mg GLA per capsule in the form of triglyceride GLA, or any appropriate salt of GLA, such as the lithium or calcium or magnesium or zinc or potassium salts.

2. Administration of 100 mg to 2,000 mg of EPA per day in the form of soft or hard gelatin capsules or tablets providing:

a. 90 to 180 mg per capsule of EPA in the form of cold water marine fish oil.

b. 200 to 600 mg per capsule of EPA in the form of an enriched EPA oil.

c. 400 to 1,000 mg of EPA per capsule in the form of triglyceride EPA or any appropriate salt of EPA such as the lithium or calcium or magnesium or zinc or potassium salts.

3. Administration of DGLA in a dose of 100 mg to 2,000 mg per day in the forms of 1 c above.

4. Administration of GLA or DGLA in association with EPA, with or without DHA, for example as 40 to 80 mg GLA per capsule in the form of evening primrose oil together with 10 mg to 100 mg per capsule of EPA in the form of cold water marine fish oil.

5. Administration of GLA or DGLA in the form of a soluble powder or effervescent granule formed from any appropriate salt of GLA as in 1c above and excipients such as citric acid monohydrate, sodium bicarbonate or other dibasic acids such as tartaric or maleic acid plus sweeteners such as sucrose or sorbitol and flavourings.

6. Administration of GLA or DGLA in the form of liquid evening primrose, borage or other appropriate oil as the oil itself or as a whip or emulsion prepared with appropriate flavors and stabilisers.

7. Administration of EPA or DHA in any appropriate chemical form, microencapsulated using starch, gelatin, gum arabic or other appropriate formulation.

8. Administration of GLA in the form of pessaries, suppositories, skin patches or any other appropriate route.

What we claim is:

1. A method of treating or preventing ectopic calcium deposition in soft tissue of blood vessels, cornea, conjunctivae, skin and brain in humans or animal in need thereof by administering one or more essential fatty acids of the n-6 and n-3 series selected from the group consisting of gamma-linolenic acid, dihomo-gamma-linolenic acid, arachidonic acid, adrenic acid, 22:5 delta-4,7,10,13,16, stearidonic acid, 20:4 delta-8,11,14,17, eicosapentaenoic acid, 22:5 delta-7, 10,13,16,19 and docosahexaenoic acid, wherein the essential fatty acids are administered as such or in salt or other pharmacologically acceptable form.

2. The method according to claim 1 where the close range of the essential fatty acid administered is from 0.01 to 1,000 mg/kg/day.

3. The method according to claim 2 wherein the dosage range administered is 0.5 to 50 mg/kg/day.

4. The method according to claim 3 wherein the dosage range administered is 2 to 30 mg/kg/day.

5. The method according to claim 2, wherein the fatty acid is administered in unit dosage form.

* * * * *